United States Patent [19]

Singer et al.

[11] Patent Number: 5,252,102
[45] Date of Patent: Oct. 12, 1993

[54] ELECTRONIC RANGE OF MOTION APPARATUS, FOR ORTHOSIS, PROSTHESIS, AND CPM MACHINE

[75] Inventors: Robert D. Singer, Clive; Ernest A. Trickey, Des Moines, both of Iowa

[73] Assignee: ElectroBionics Corporation, Ankeny, Iowa

[21] Appl. No.: 926,485

[22] Filed: Aug. 5, 1992

Related U.S. Application Data

[63] Continuation of Ser. No. 301,539, Jan. 24, 1989, abandoned.

[51] Int. Cl.$^5$ ................................................ A61F 2/48
[52] U.S. Cl. .................................... 623/24; 623/26; 128/25 R
[58] Field of Search ...................... 623/24–25, 623/26, 64, 66; 128/25, 26

[56] References Cited

U.S. PATENT DOCUMENTS

| | | |
|---|---|---|
| 3,323,518 | 6/1967 | Swanson . |
| 3,418,662 | 12/1968 | Bottomley . |
| 3,491,378 | 1/1970 | Ioffe et al. ............... 623/25 |
| 3,631,542 | 1/1972 | Potter . |
| 3,722,005 | 3/1973 | Cowland . |
| 3,735,425 | 5/1973 | Hoshall et al. . |
| 3,769,636 | 11/1973 | Friedman . |
| 3,987,498 | 10/1976 | Mason . |
| 4,314,379 | 2/1982 | Tanie et al. . |
| 4,319,864 | 3/1982 | Kaufeldt ............... 901/23 |
| 4,323,060 | 4/1982 | Pecheux . |
| 4,537,083 | 8/1984 | Saringer . |
| 4,571,750 | 2/1986 | Barry . |
| 4,575,297 | 3/1986 | Richter . |
| 4,637,379 | 1/1987 | Saringer . |
| 4,644,938 | 2/1987 | Yates . |
| 4,665,900 | 5/1987 | Saringer . |
| 4,685,928 | 8/1987 | Yaeger ............... 623/25 |
| 4,711,450 | 12/1987 | McArthur ............... 272/130 |
| 4,716,889 | 1/1988 | Saringer . |
| 4,808,187 | 2/1989 | Patterson et al. ............... 623/25 |
| 4,825,852 | 5/1989 | Genovese . |
| 4,842,265 | 6/1989 | Kirk . |
| 4,875,469 | 10/1989 | Brook et al. ............... 128/26 |
| 4,930,497 | 6/1990 | Saringer . |
| 4,934,694 | 6/1990 | McIntosh ............... 272/125 |

OTHER PUBLICATIONS

"A Progress Report on a Programmed Orthotic Arm", Babnick et al., Jun. 1963, pp. 509–517.
"A Newly Created Electrical Total Arm Prosthesis of Module Type Controlled by Microcomputer and Voice Command System", Funakubo, 1981, pp. 45–47.
"Application of External Power in Orthotics" by Hans Richard Lehneis (Sep. 1968).
"Upper-Limb Orthotics" by H. Richard Lehneis, pp. 14–20.
"Upper Limb Powered Components and Controls: Current Concepts" by John W. Miehael (1986), pp. 66–77.
"Current Concepts Review Myoelectric Prosthesis" by Alfred Kritter (1985), pp. 654–657.
"Development of the Utah Artificial Arm" by Jacobsen et al., vol. BME-29 No. 4, Apr. 1982, pp. 249–269.
"Clinical Experience With the Utah Artificial Arm" by Sears et al., (1984), pp. 30–33.
"The Boston Elbow", 3 pages.
Variety Model VV3-8 Electric Elbow by Variety Ability Systems, Inc., pp. 1–5.

(List continued on next page.)

Primary Examiner—Randall L. Green
Assistant Examiner—Gina M. Gualtieri

[57] ABSTRACT

A therapeutic electronic range of motion apparatus includes a remote subsystem for generating motion commands which are transmitted to a local subsystem at an orthosis, prosthesis or CPM machine. The local subsystem includes a local controller for controlling and monitoring the position, speed, and direction of an actuator which moves an orthotic brace, prosthesis or CPM machine mounting. The apparatus is programmable enabling a patient to program stopping positions which thereafter are selectable by command. When the actuator is not in motion the local controller enters a sleep mode to conserve power. The controller is automatically awakened when a motion command is received.

12 Claims, 19 Drawing Sheets

OTHER PUBLICATIONS

Elbow C.P.M. Machine by Kinetec, pp. 1–13.

Mobilimb TM Upper Limb CPM Units, 11 pages.

"Motorized Leg Exerciser 3080. S"by Kinetec, 20 pages.

Brochure Published by Toronto Medical, entitled, "Mobilimb S2 Shoulder CPM".

Brochure Published by Toronto Medical entitled, "Mobilimb E2 Elbow CPM".

Brochure Published by Danninger Medical Technology, Inc., entitled, "Model 300 Danni-Flex".

Brochure by Biomedical Equipment Rental & Sales Inc., entitled, "Introducing Mobilimb, the Original Continuous Passive Motion Concept".

Brochure by Toronto Medical entitled, "Mobilimb L2 Lower Limb CPM".

Instruction Manual for Model 300 Danni-Flex Continuous Passive Motion Machine.

Danniflex 400 Continuous Passive Motion System Operating Instruction Manual.

Brochure entitled, "Danniflex CPM 500" by Danninger Medical Technology Inc.

Brochure entitled, "Artromot the Modular CPM Program for Joint Mobilization", by Thera Kinetics, Inc.

User's Manual by Cogemo S.A. Constructeur, entitled "Motorized Leg Exerciser 3080.S User's Manual".

User's Manual by Cogemo, S.A., Tournes, France entitled "Kinetic Elbow CPM Machine".

I.E.E.E. Transactions on Biomedical Engineering vol. BME-34, No. 9, Sep. 1987, pp. 724–736, New York, U.S.; C. Abul-Haj et al.: "An Emulator System for Developing Improved Elbow-Prosthesis Designs".

Medical & Biological Engineering & Computing vol. 27, No. 6, Nov. 1989, pp. 549–556, Stevenage, Herts, GB; R. H. Nathan et al.: "An FNS-based system for generating upper limb function in the C4 quadriplegic".

US-A-3 418 662 (Bottomley et al.).

EPO Search Report 90 10 1327. IEEE/Seventh Annual Conference of the Engineering in Medicine and Biology Society vol. 2, Sep. 1985, pp. 649–652, Chicago, U.S.; D. T. Gibbons et al.: "An above-elbow Prosthesis Employing Programmed Linkages".

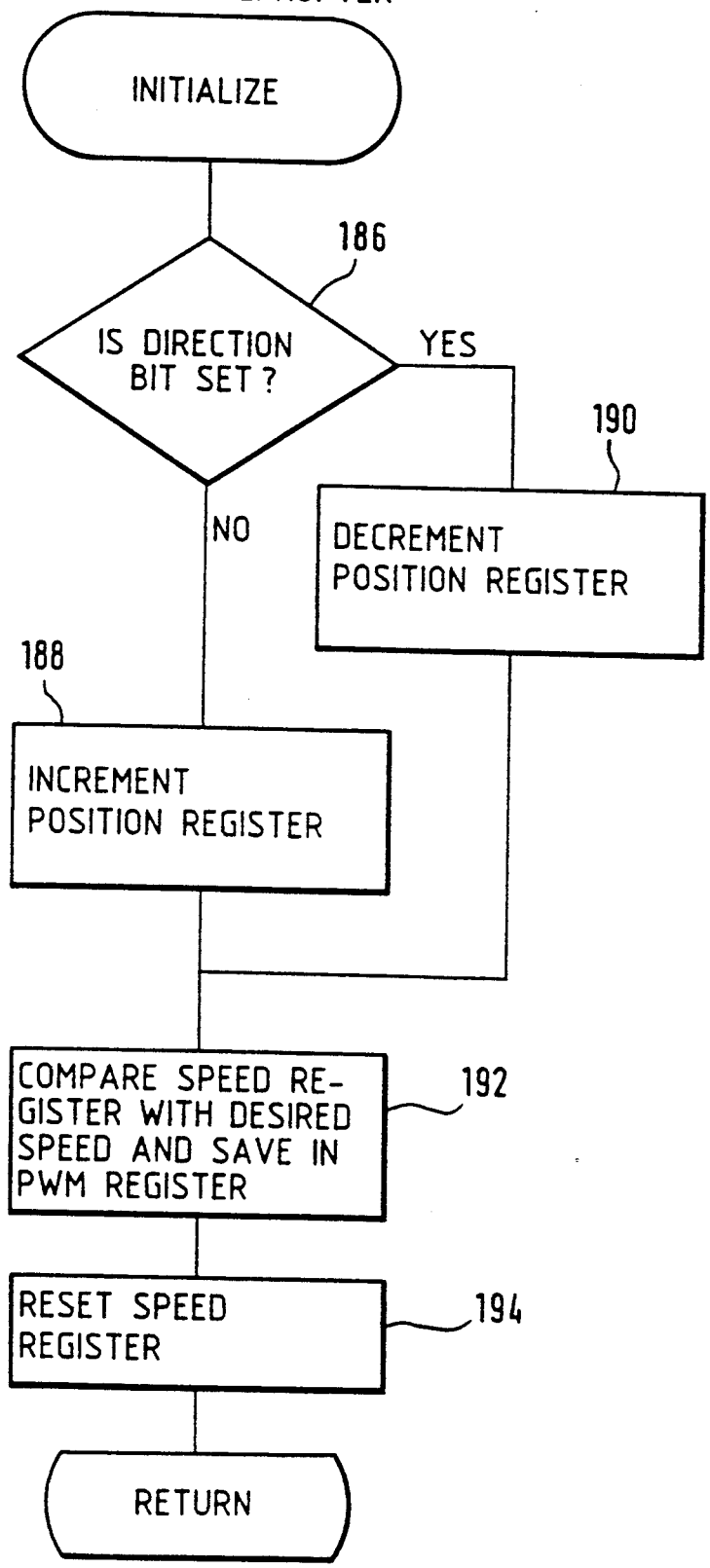

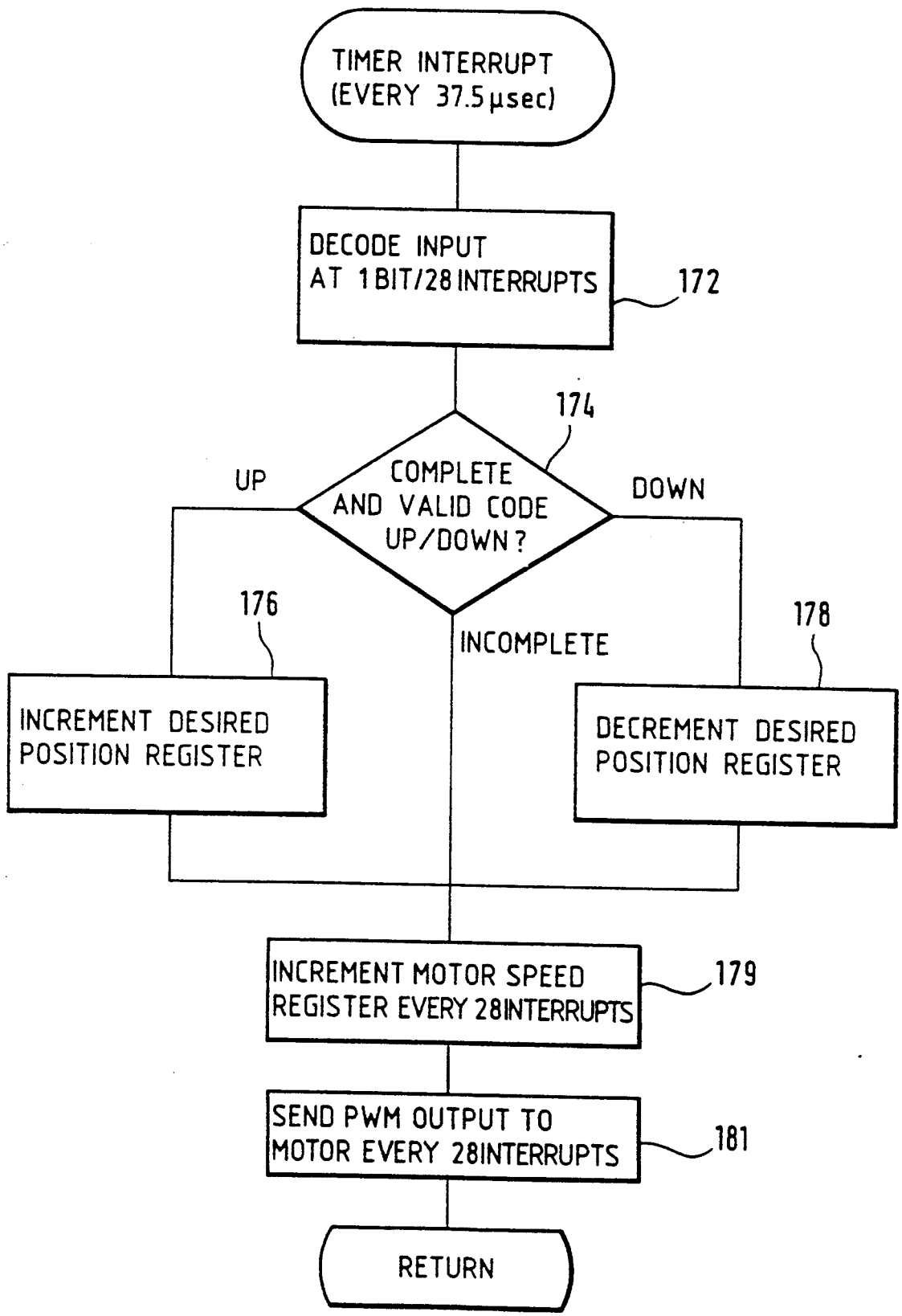

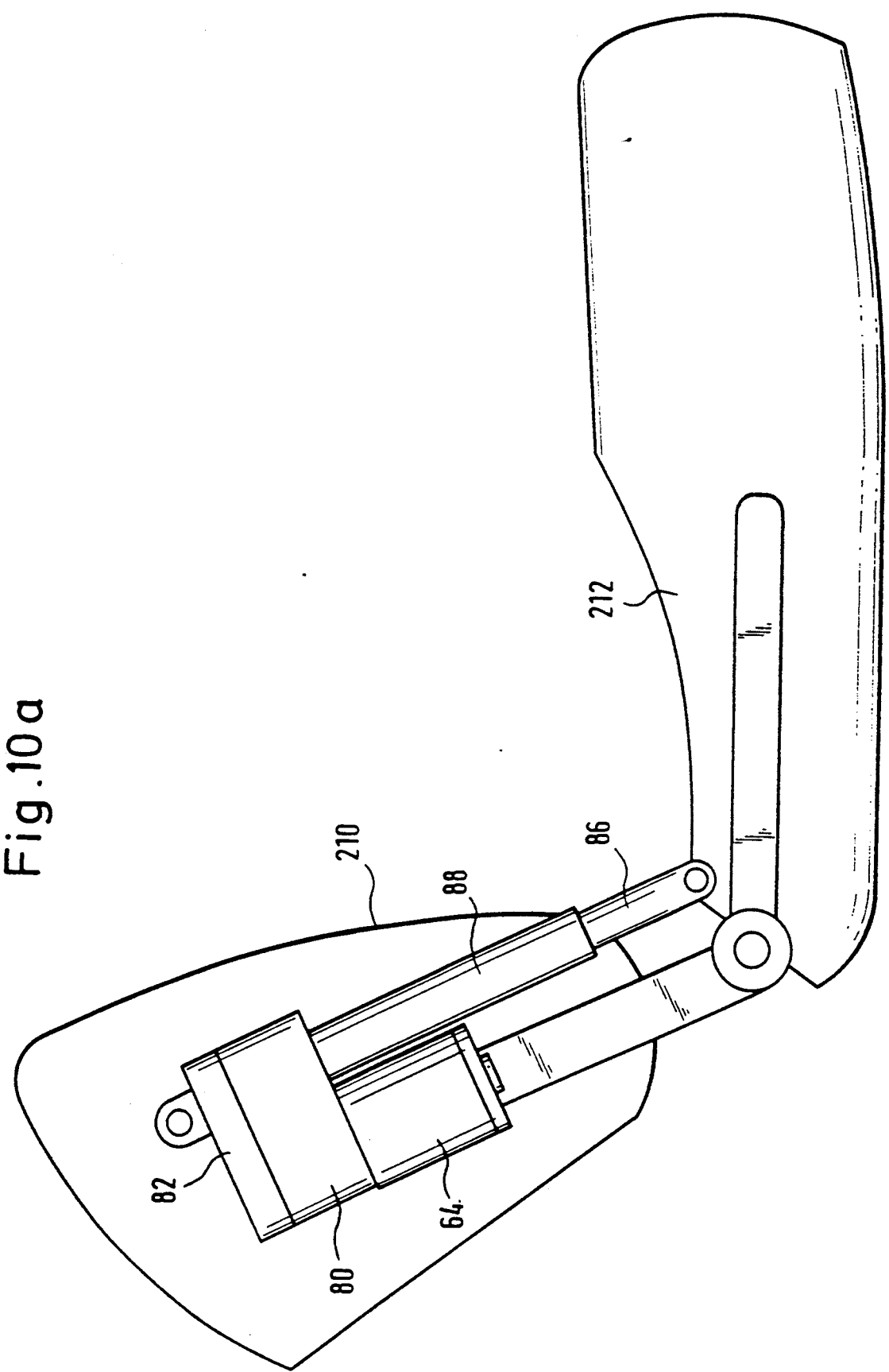

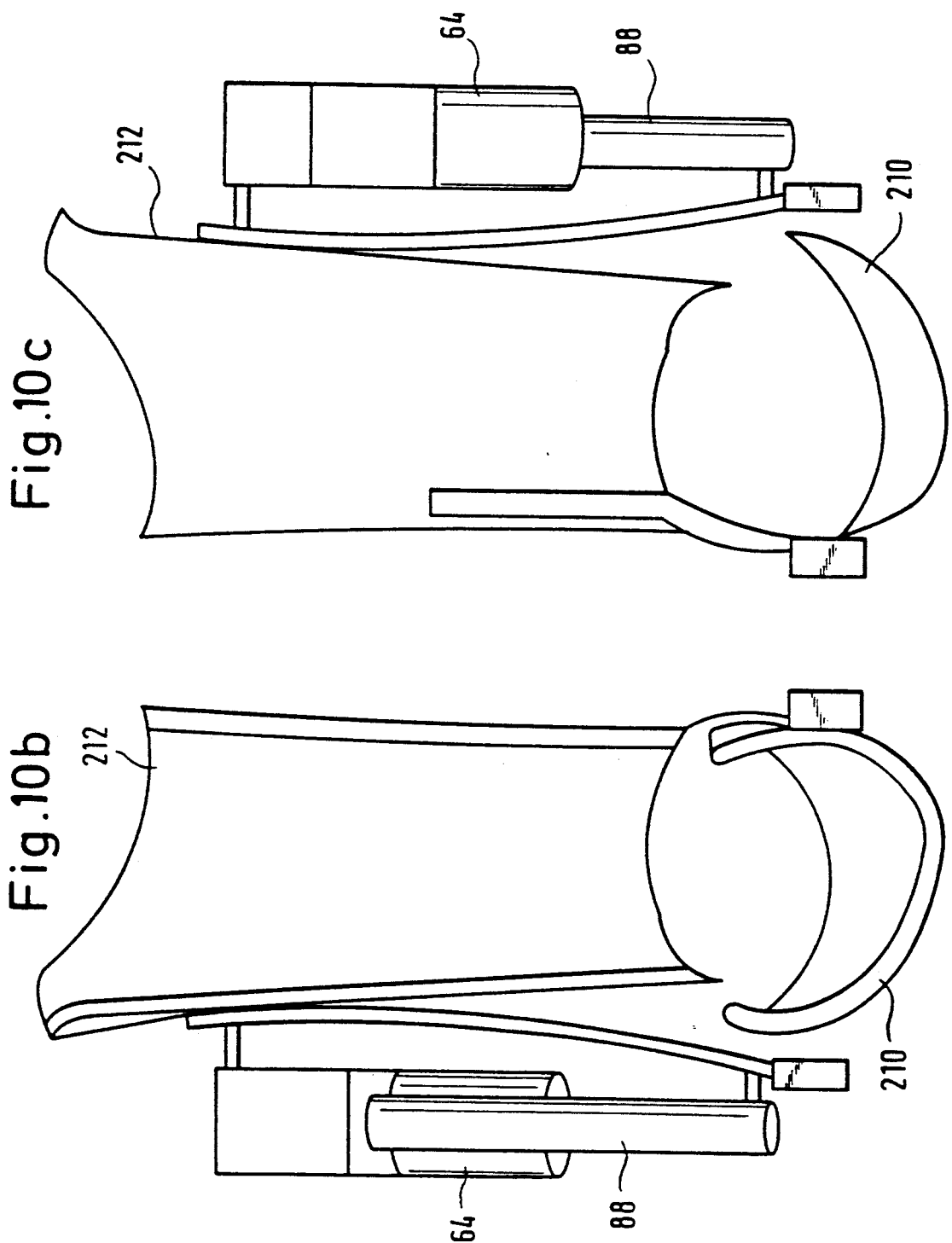

ELECTRONIC RANGE OF MOTION APPARATUS, FOR ORTHOSIS, PROSTHESIS, AND CPM MACHINE

This is a continuation of co-pending application Ser. No. 07/301,539 filed Jan. 24, 1989, now abandoned.

FIELD OF THE INVENTION

This invention relates to an electronic range of motion apparatus for motorized control of a human or artificial limb's position. More particularly this invention relates to a user-programmable electronic range of motion apparatus having multiple range capability for use as an orthosis, prosthesis or continuous passive motion machine.

BACKGROUND

The electronic range of motion apparatus of this invention is adapted for use as or with an elbow, knee, wrist or ankle and relates to orthoses, prostheses and continuous passive motion (CPM) machines.

With regard to orthotic elbow devices, non-powered mechanical systems, of a ratchet-lock joint design are the most common. In such design, a spring-loaded pawl, for example, engages a tooth of the ratchet wheel when the joint is flexed. The pawl is released by flexing the joint to its maximum or by a shoulder or finger controlled cable.

Another common elbow orthosis is a "dorsal elbow flexor orthosis". This orthosis is used in cases where an elbow must be stabilized orthotically at a desired degree of flexion-extension, with the ability to adjust the flexion-extension setting as the patient progresses through rehabilitation. It is non-electronic and only serves to stabilize the elbow at the desired degree of flexion-extension. The orthosis is not designed or intended to provide articulated motion as does this invention. The degree of flexion-extension of the "dorsal elbow flexer orthosis" typically is attained by rotating a screw turn-buckle assembly.

Other orthotic devices include powered elbow orthotic devices, which typically incorporate a $CO_2$ piston and cylinder actuator. Such devices are cumbersome and require the wearing of a shoulder harness to hold the elbow control mechanism in place.

It is an object of this invention to provide an electronic range of motion apparatus for an elbow orthosis which does not require application of a harness and may fit under a patient's shirt sleeve.

With regard to prostheses, the Utah Arm TM is representative of a state-of-the-art prosthetic elbow. Such prosthesis is an electronic battery powered above-elbow prosthesis that is myoelectrically controlled. Position locking of the elbow assembly is accomplished via a sliding member located in the elbow molding, which engages an aluminum circumferential locking ring which is insert-molded into the forearm structure. The circumferential locking ring contains detent holes which allow the arm to be locked in 21 positions.

The elbow component is operated by a dc motor that drives a gear train/clutch system, which rotates an output shaft into two positions 180 degrees apart. The output shaft is connected to a spring, such that in each of its two rotational positions, the locking member is spring-biased to be in the locked or unlocked position.

Prosthetic elbows typically are either passive, body-powered, cable controlled, or myoelectrically controlled. Prosthetic devices including the Utah Arm TM are non-processor controlled, either myoelectrically or mechanically operated, and offer between 8 and 21 fixed locking positions.

It is an object of this invention to provide a processor controlled apparatus for orthotics and prosthetics.

It is another object of this invention to provide an electronic range of motion apparatus having a screw-jack type actuator that is infinitely variable and locking in approximately 200 positions in the normal range of 140 degrees of travel from full-extension to full-flexion.

It is another object of this invention to provide an electronic range of motion apparatus having a user-programmable microcontroller enabling programming of stop positions by the user.

It is another object of this invention to provide a wireless remote control system enabling convenient operation and control by the user. Previously locking flexion-extension positions could not be altered or changed by the patient.

Continuous Passive Motion (CPM) machines are powered therapy devices that move a patient's affected joint (elbow, knee, shoulder, or other) through a controlled range of motion. Simply stated, a CPM machine is a therapy machine that is used for gentle muscle stretching, or following surgery to rehabilitate the joint. Prior CPM machines have been large and cumbersome.

It is an object of this invention to provide a portable CPM machine for use outside the hospital or rehabilitation center providing flexion and extension for a joint or a human limb by controlled articulation of the affected joints and muscles.

SUMMARY OF THE INVENTION

These and other objects of the invention are accomplished by an electronic range of motion apparatus adapted for an orthosis, prosthesis or CPM machine. The range of motion machine includes a local controller for controlling the speed, position and direction of motion of an actuator via an electric motor and transmission gears. The local controller is programmable by the user to define stop positions of the actuator during flexion or extension. Photosensors are used to sense the actuator movement and feedback signals to the local controller so as to control the actuator speed and position. Nonvolatile memory is included so that the stop positions are saved even when the machine is turned off.

During normal use, a user operates a switching mechanism such as a voice-actuated switch, mechanical switch, or myoswitch to cause the actuator to move to a specific stop position in a specific direction. The inputs from the automatic switching mechanism are fed to a remote controller which in turn feeds the signals to the local controller via an RF transmitter and an RF receiver.

This invention may be used to gradually increase the patient's flexion and extension ability with gentle stretching utilizing the self-programmable feature and multiple range options.

A preferred embodiment described is an elbow orthosis for external control of an elbow which, for example, has flaccid paralysis but retains significant range of motion. This occurs in a variety of medical conditions including partial and complete brachial plexus injuries, traumatic and disease related nerve palsies, and certain neuromuscular diseases such as polio and muscular dystrophy. In the ideal circumstance, the hand will retain some sensation and some useful function, and the primary loss will be the ability to voluntarily flex and extend the elbow. Prior to the development of this invention flexion and extension had been restored using mechanical components with less than 15 locking positions. Control mechanisms required mechanical harnessing or the use of electrical wires, resulting in a cumbersome device.

This invention may also be applied for the treatment of individuals with more generalized paralysis of the arms as well as other parts of the body. Such individuals may have spinal cord injuries, or more severe neurological defects. Where additional arm paralysis is present, the invention may be combined with conventional hand and wrist bracing depending upon the patient's particular medical condition.

BRIEF DESCRIPTION OF THE DRAWINGS

FIGS. 9a-h are flow charts of the Local Controller software.

FIGS. 10a-c are lateral, anterior and posterior views of the mechanical assembly of FIG. 7 adapted on an orthotic brace.

DETAILED DESCRIPTION

Figure 1:
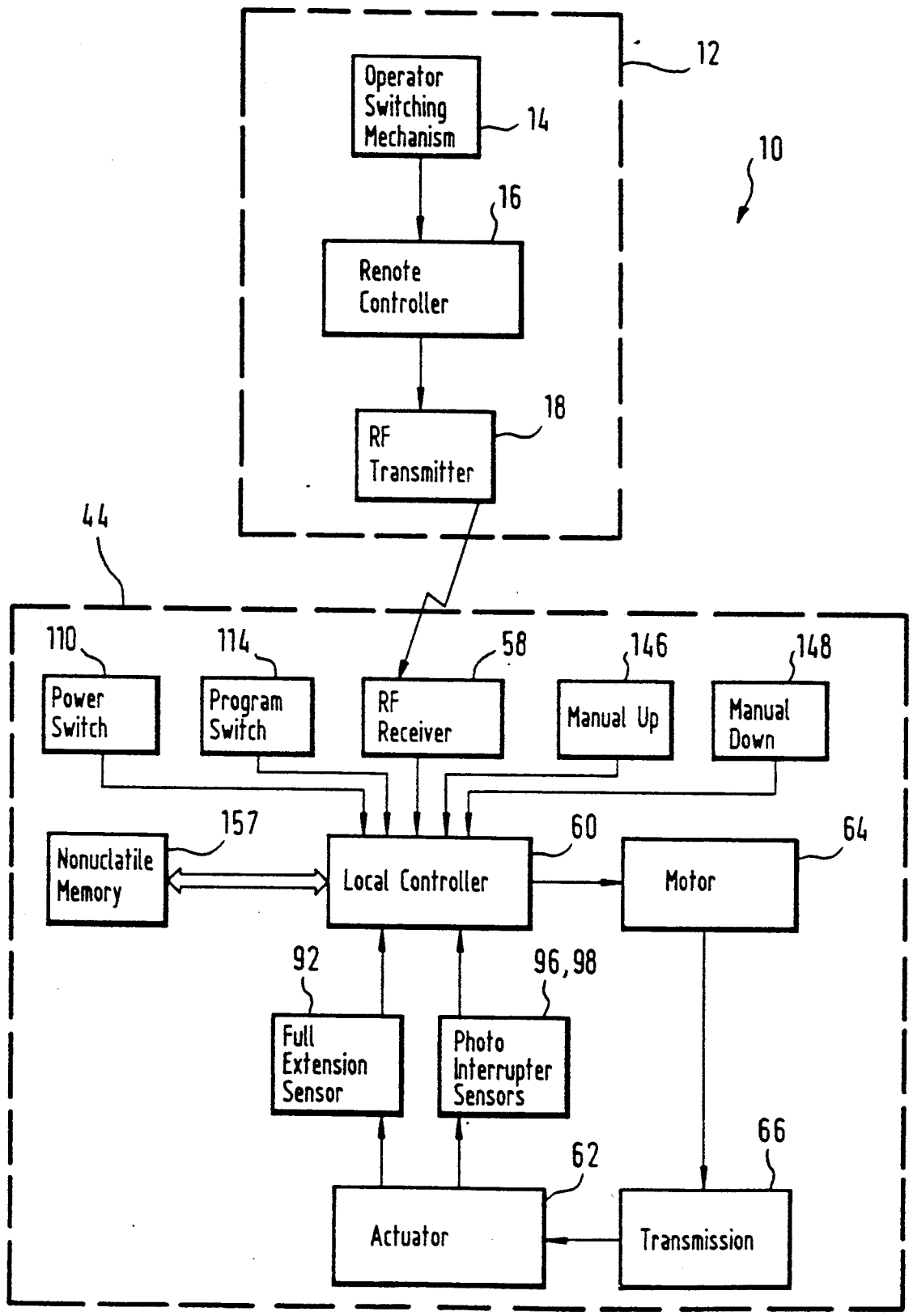
FIG. 1 is a block diagram of the electronic range of motion apparatus of this invention.

A block diagram of the preferred embodiment of the range of motion apparatus 10 is shown in FIG. 1. A remote subsystem 12 includes an operator switching mechanism 14, a remote controller 16, and an RF transmitter 18. The operator switching mechanism may be a voice-actuated switch, a mechanical switch, or a myoswitch. The remote controller 16 monitors the operator switching mechanism 14 for commands to move the actuator. The operator may generate sequential "up" commands or "down" commands through the operator switching mechanism 14 to control the direction and degree of movement of the orthosis.

Figure 2A:
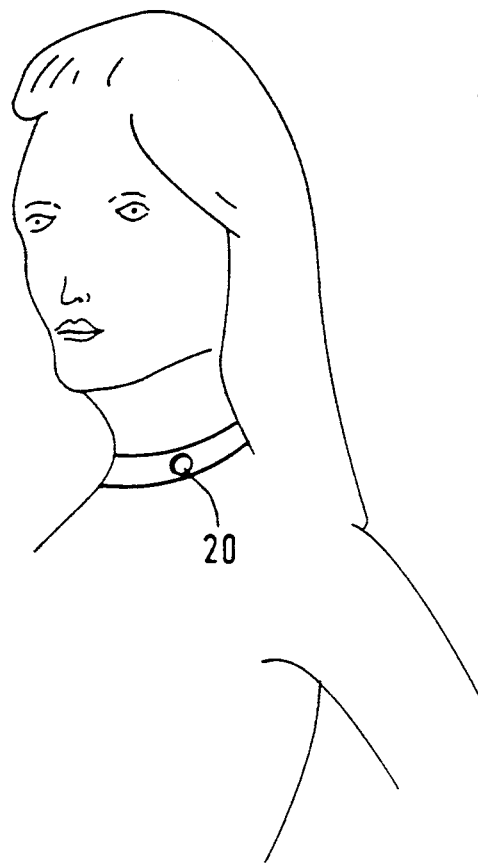
FIGS. 2a-b are diagrams of a voice activated embodiment of the automatic switch mechanism.
Figure 2B:
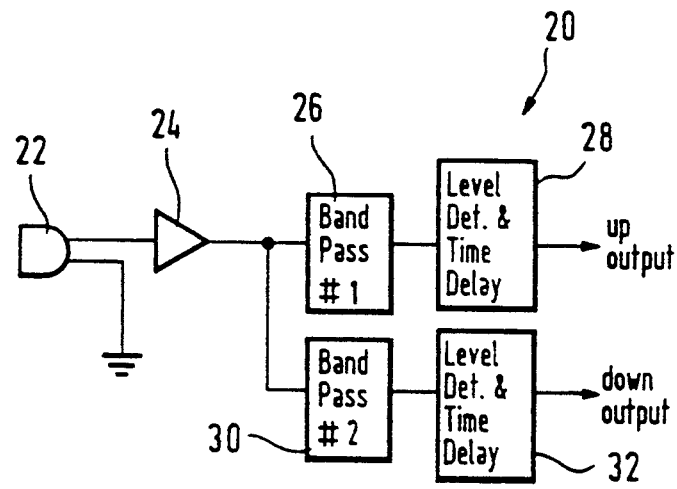

Referring to FIGS. 2a and 2b, a voice actuated switch 20 and corresponding electrical block diagram is shown. The switch 20 may be positioned about the neck to pick up sound waves through transducer 22. The sound waves are converted into electrical signals by the transducer 22, then amplified by preAmp 24. The amplified signal is input to two channels, one channel for detecting an "up" command, the other channel for detecting a "down" command. In the first channel, bandpass filter 26 filters the amplified signal. For the appropriate voice command, voltage level detector and time delay circuit 28 outputs an "up" command signal to the remote controller 16. Similarly, in the second channel band-pass filter 30 filters the amplified signal. Again for the appropriate voice command, voltage level detector and time delay circuit 32 outputs a "down" command signal to the remote controller 16.

Figure 3:
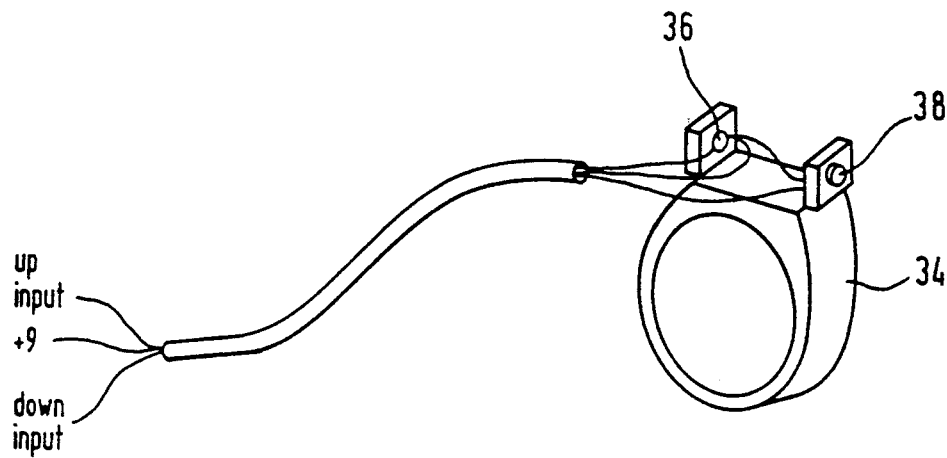
FIG. 3 is a diagram of a mechanical switch embodiment of the automatic switch mechanism.

Referring to FIG. 3, a mechanical switch 34 may be worn as a ring and operated with a 9 $V_{dc}$ voltage source. The switch 34 includes a first button 36 for generating an "up" command signal and a second button 38 for generating a "down" command signal. The respective "up" or "down" command signals are received by the remote controller 16.

Figure 4:
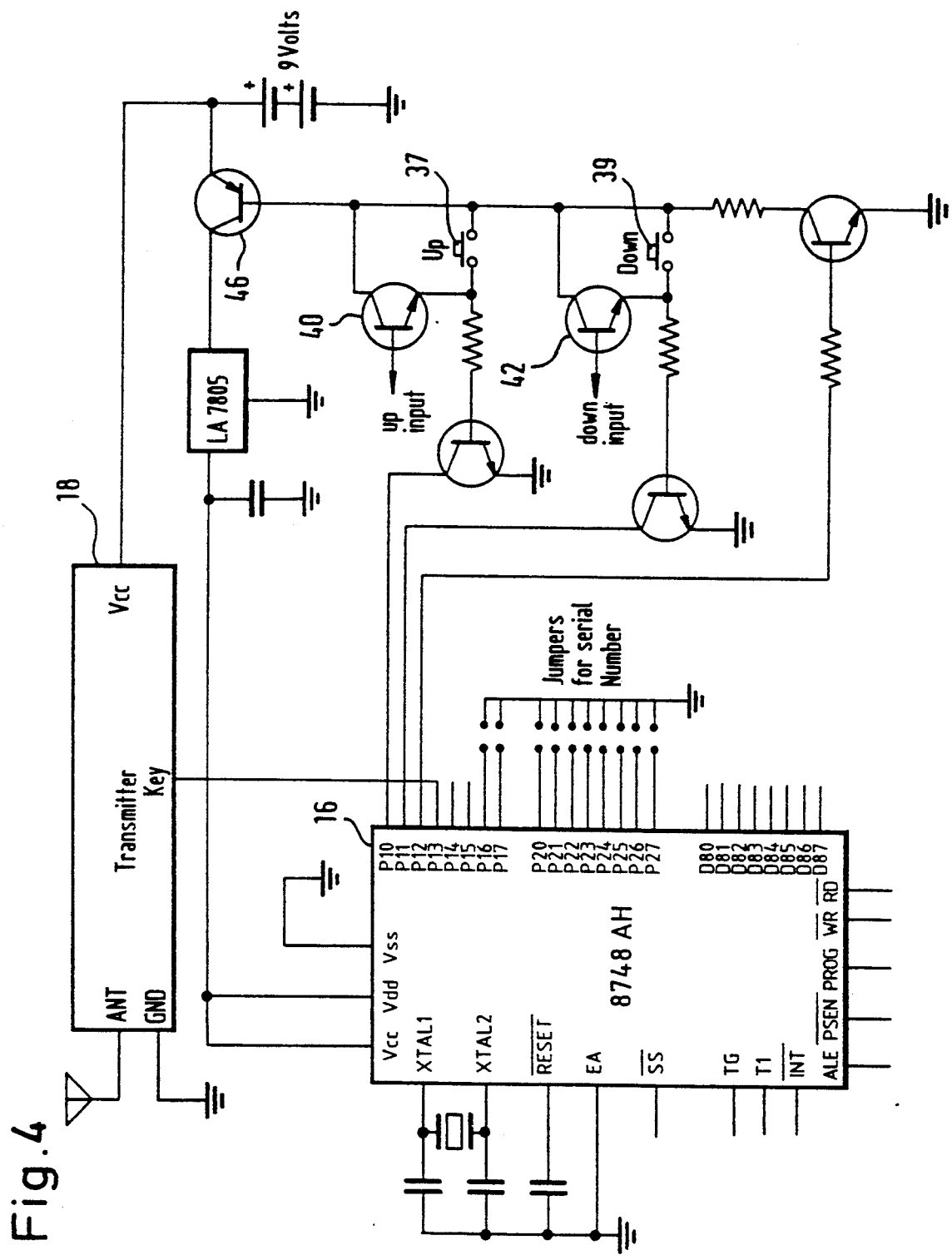
FIG. 4 is a schematic of the remote controller and RF transmitter circuits.

As illustrated in FIG. 4, an electrical up input is received at transistor 40 from, for example, a voice actuated switch 20 (such as from the level detect and time delay 28 of FIG. 2b), mechanical up switch 36 (see FIG. 3) or a myoelectric sensor (not shown). Similarly the down input is received at transistor 42 from a voice actuated switch 20, mechanical down switch 38 or a myolectric sensor. In addition, switches 37 and 39 are located at the remote processor assembly to provide convenient back-up switches for entering an up command or down command.

The remote controller 16 may be an 8748AH microprocessor, although other microprocessors may be used. Controller 16 turns on the radio transmitter 18 causing the transmission of an encoded signal to the local subsystem 44 (see FIG. 1). The radio transmitter 18 is a low-power VHF transmitter modulated with digital data generated by the remote controller 16.

The encoded signal is in the form of a 16 bit word that corresponds to a particular function. The first ten (10) bits correlate to the last three digits of a given serial number for a specific apparatus 10. The serial number is included in the encoded signal to ensure that the radio transmission from one unit will not activate another unit when two units are in close proximity and the prevent the local controller 60 from being activated by random electrical magnetic interference (EMI). The next six (6) bits offer a choice of 64 operational codes. Referring to FIG. 4, a jumper may be used to hardwire the serial number.

When an input is received by transistor 40 or 42, base current is provided to transistor 46 putting it into an "on" state. Transistor 46 then provides power to microprocessor 16. The processor 16 checks pins P10 and P11 to determine whether the input is an "up" or "down" input.

After the encoded signal is transmitted, the remote controller 16 goes into a power down mode and turns off the radio transmitter 18 to conserve battery life while waiting for the next operator command. A bit (P12 of microprocessor 16 in FIG. 4) is set to retain power switching transistor 46 in an "on" state while the microprocessor 16 sends the 16 bit serial code by P13 to the transmitter 18 key input. There is a short delay while the microprocessor waits from an up or down input on P10 or P11. If no input is received after a period of time, P12 goes to a "0" state which puts transmitter 46 in an off state, thereby removing power to the processor 16 putting itself to sleep.

Figure 5:
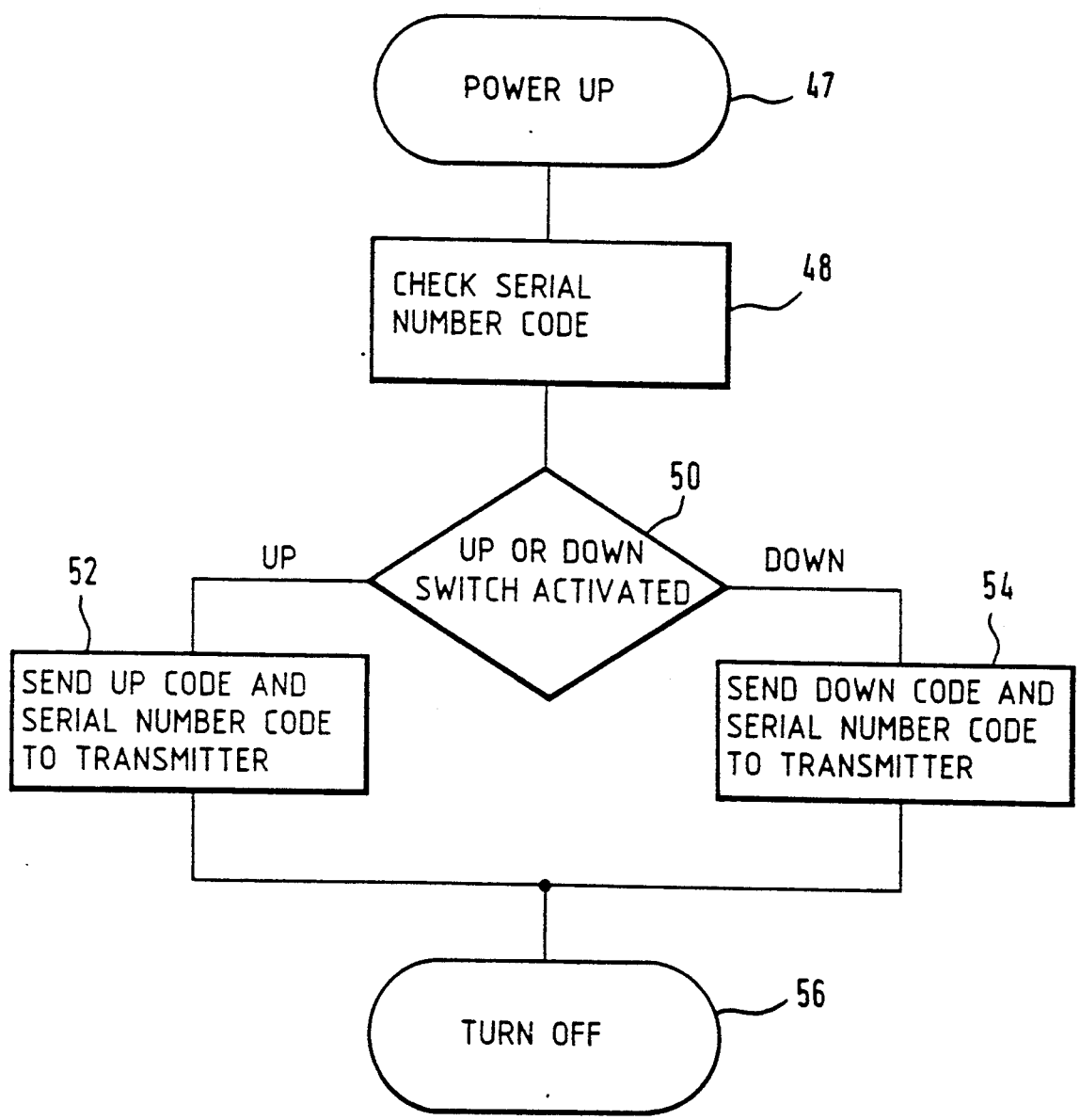
FIG. 5 is a flow chart of the remote controller software.

A flowchart for the software of remote controller 16 is shown in FIG. 5. When the operator switching mechanism 14 is activated, the power up of remote controller 16 is triggered as step 47. The hardwired apparatus serial number then is read at step 48 from bits P16-P27 (see FIG. 4). The controller 16 then reads the operator command at step 50. If an "up" command is received, step 52 is executed causing an encoded signal of the "up" command and serial number to be output to the transmitter 18 for transmission to the local subsystem 44. If a "down" command is received, step 54 is executed causing an encoded signal of the "down" command and serial number to be output to the transmitter 18 for transmission to the local subsystem 44. The controller 16, then goes into a power down mode at step 56 as previously described.

Because the apparatus 10 is wireless, simple interchange of a variety of control options is possible from various parts of the body, which do not necessarily need to be in close proximity to the affected limb.

Figure 6:
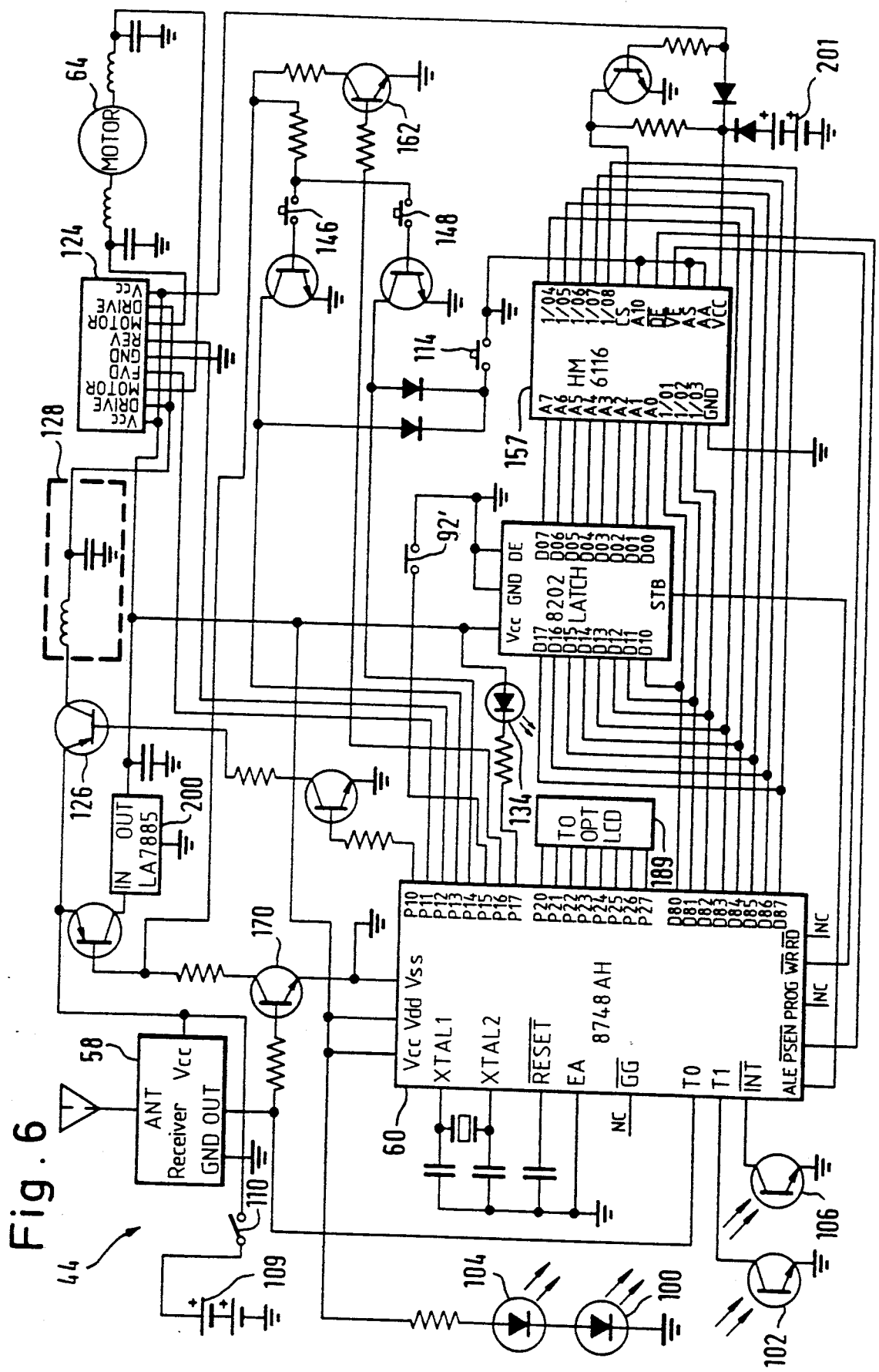
FIG. 6 is a electrical schematic of the local controller, receiver and motor circuits.

Referring to FIGS. 1 and 6, the local subsystem 44 includes an RF receiver 58 for receiving the encoded signal and a local controller 60 for processing the encoded signal.

The receiver 58 is a tuned RF receiver which detects the encoded signal from the transmitter 18 and outputs encoded digital data to the local controller 60. The local controller 60 may be an 8748AH microprocessor, although other microprocessors may be used. Preferably, the local controller 60 is capable of receiving 64 different encoded signals, thus allowing for a variety of functions and sophisticated control designs.

The local controller 60 provides three functions, two during normal operation. First, the local controller 60 interprets the encoded digital data input from the radio receiver 58 to identify whether an "up" command or a "down" command is received. Second, it controls the position and speed of the linear actuator 62. The third function, the function which does not occur during normal operation, is the operation of a "learn mode" during which the operator can program flexion-extension stop points for the actuator's movement. Stop positions may be programmed from a range of approximately 200 positions.

Figure 7:
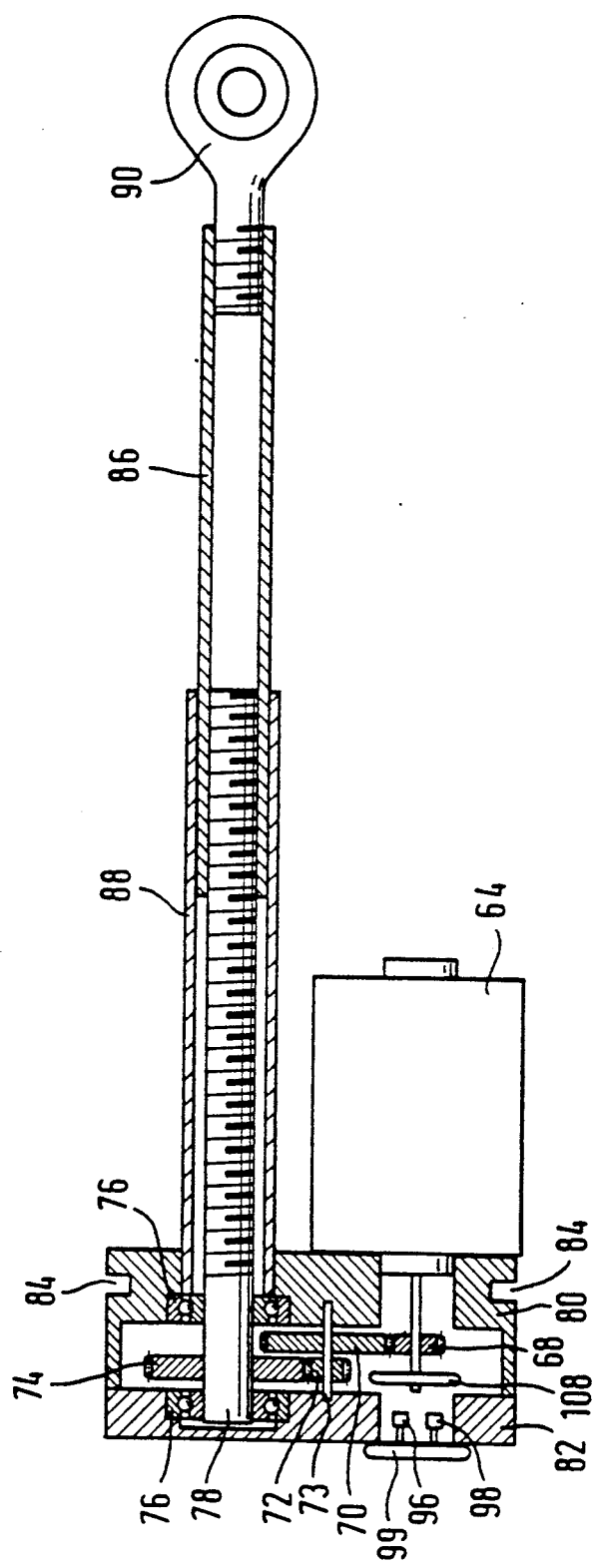
FIG. 7 is a sectional view of the motor-transmission-actuator mechanical assembly.
Figure 8:
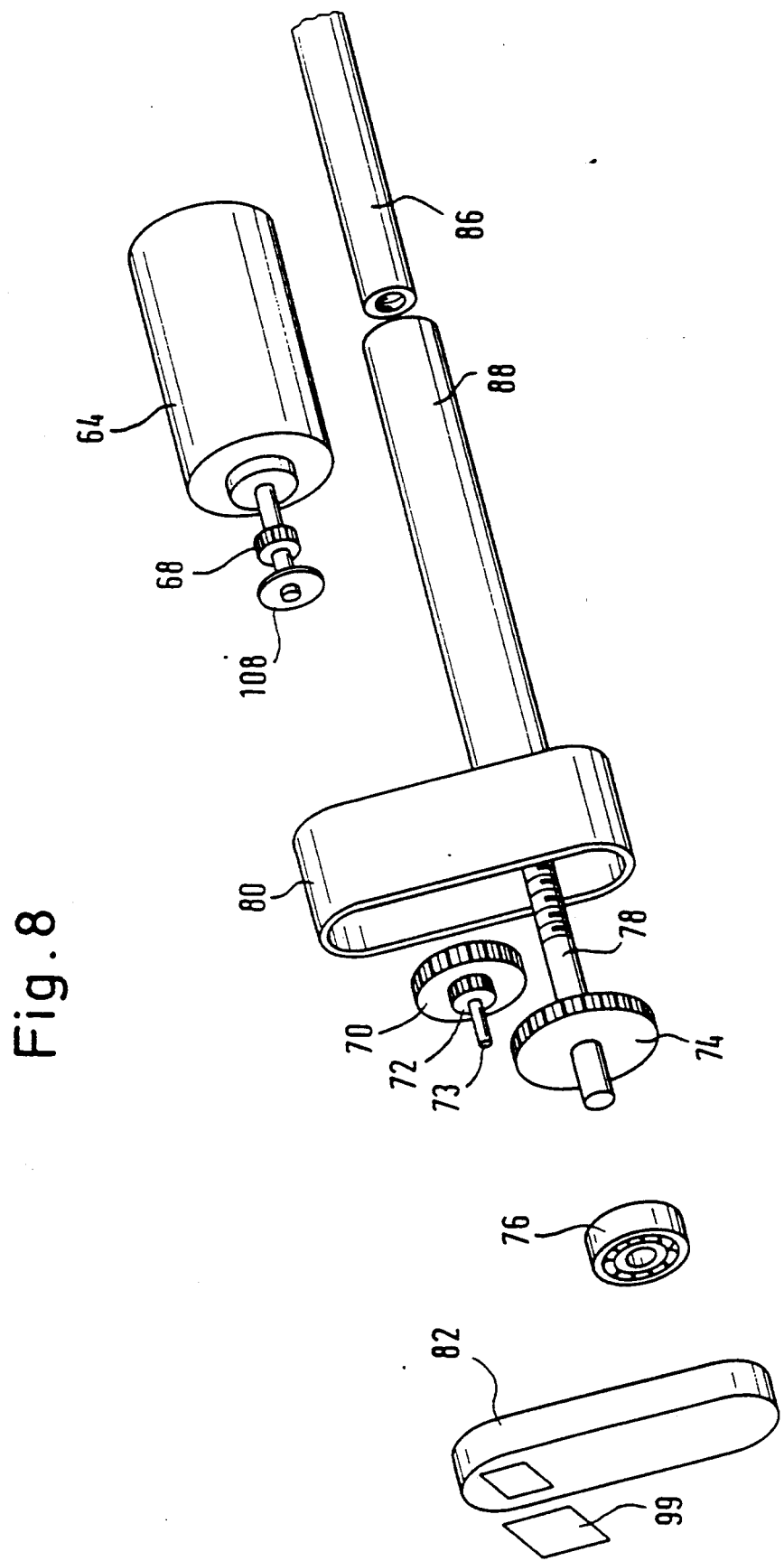
FIG. 8 is an exploded view of the mechanical assembly of FIG. 7.

Referring to FIG. 1, the actuator 62 is under local controller 60 control via motor 64 and transmission 66. Referring to FIGS. 7 and 8, the motor-transmission-actuator mechanical assembly is shown in plane and exploded views. The motor 64 may be a permanent magnet direct current motor with conventional brush and commutator for commutating the current through the armature. The transmission 66 is a two-stage reduction system. In the first stage, a 10 tooth pinion gear 68 on the motor 64 drives a 32 tooth drive gear 70 to provide a 3.2 gear reduction. Drive gear 70 is connected to another 10 tooth pinion gear 72 by gear shaft 73 which in turn-drives a 44 tooth idler gear 74 mounted on the actuator lead screw 78, to provide a gear reduction of 4.4 in the second stage. The overall gear reduction for the transmission 66 is 14.08 although other gear reductions and transmission assemblies may be used.

Ball bearings 76 hold the lead screw 78 inside the transmission case 80 and are mounted on the lead screw 78 to accommodate the high thrust loads incurred during operation. The transmission case 80 has a cover 82 and gimbal holes 84 for attachment to an orthosis or prosthesis or CPM machine mount.

The actuator 62 includes a lead screw 78 received into one end of a ram 86 within a ram housing 88. A helm ball joint 90 (shown only in FIG. 7) is received into the other end of ram 86. The ram is constructed of three-eighth inch diameter stainless steel. The lead screw 78 is made of brass having approximately 28 threads per inch. The lead screw turns at 300-1500 revolutions per minute, fast enough to move the brace the full length of travel in approximately 2 seconds. Other materials and constructions, however, may be used.

The actuator 62 is oriented for the line of the lead screw 78 to intersect the attachment points 84, 90 to minimize binding forces in the assembly. The proximal attachment point 84 is a gimbal, while the distal attachment point is a helm ball joint 90. By using ball and gimbal type attachments, the attachment points are self aligning.

Referring again to FIGS. 1 and 6, a full extension sensor 92, embodied as a mechanical down limit switch 92', senses that the ram 86 has reached the end of its extension. The local controller 60 uses this signal to indicate a 'zero' or reference position of actuator 62.

Two photo interrupter sensors 96, 98 mounted on a photo-interrupter PC board 99 (see FIG. 7) provide inputs to the local controller 60 to enable controller 60 to determine the position, speed and direction of the actuator 62. Photo interrupter sensor 96 provides a light circuit that includes a light emitting diode 100 and phototransistor 102 (see FIG. 6). The second photo interrupter sensor 98 also provides a light circuit that includes a light emitting diode 104 and a phototransistor 106. The light emitted from the respective L.E.D.s 100, 104 is reflected off a reflective portion of a photo-interrupter encoding wheel 108 and detected by the respective phototransistors 102, 106 so that two phase-related pulse trains are generated and received by the local controller 60. By detecting the phase of the two pulse streams, the controller 60 can determine whether the lead screw 78 is turning clockwise or counterclockwise (and thus whether the actuator is extending or flexing.) Using the zero point as a reference, the local controller can compute the position based on the number of pulses received by correlating (i) the number of pulses to the number of rotations of lead screw 78 and (ii) the number of rotations to the distance the actuator moved. The number of reflective surfaces, the distance between reflective surfaces in the encoder wheel and the threads per inch of the lead screw define the conversion factors. In addition, the time between corresponding pulses in the two respective pulse trains is measured to determine the speed of the actuator.

Other light circuits also may be used, such as an encoder wheel having one or more holes and an L.E.D. and phototransistor positioned on opposite sides of the wheel. In such other circuit the pulse trains are generated by the periodic passing of light through the holes in the encoder wheel.

The position of the actuator 62 is calculated by the number of revolutions the lead screw 78 turns from its home position. This value is stored in a register inside the local controller 60. As the lead screw 78 rotates, this value is incremented. The current value of the register tells the local controller 60 the position of the actuator 62. If the local controller 60 receives a command to move the actuator 62 to a new position, it will compare the desired position's value with the value that is currently in the register. If the register value is greater or less than the current position, the local controller 60 will turn on the motor in the appropriate direction of rotation to increase or decrease the value of the position until it matches the desired position. At that point the actuator 62 is stopped. It is also important to note that the controller 60 will control the speed of the actuator 62 during movement to prevent overshoot and provide a smooth motion. If the actuator 62 must travel a relatively long distance the local controller 60 will cause it to move at a relatively high speed until the actuator 62 gets close to the stopping position. The actuator 62 is then slowed to stop at the correct position.

To control the position and speed of the actuator, the controller 60 outputs three one-bit signals to the motor control integrated circuit 124 to control four drive states. The first drive state is the coast state where no electrical force is applied to the motor. The second drive state is left rotation for the up (flexion) direction. The third drive state is the right rotation for the down (extension) direction. The fourth drive state is electrodynamic braking. The three signals output to motor control circuit 124 are (1) forward, (2) reverse, and (3) pulse width modulated drive speed voltage. In the coast state neither the forward nor the reverse signals are active. In the up state the forward signal and the drive speed voltage signal control the speed and movement. In the down state the reverse signal and the drive speed voltage signal control the speed and movement. In the braking state, both the forward and reverse signals are high, causing the motor controller 124 to ground both leads of motor 64 providing electrodynamic braking. A combined use of drive, coast, and brake states are used to bring the actuator 62 to a smooth stop on position without overshoot.

FIGS. 9a-h show flow charts for the software of local controller 60. When the power switch 110 (see FIGS. 1 and 6) is switched on, the actuator is fully extended to the end of travel at the 'zero' or reference position at step 112. The program switch 114 (see FIGS. 1 and 6) is then polled at step 116 to determine if it is depressed. If yes, step 118 is executed and the system is operated in program mode. If not, step 120 is executed and the local subsystem 44 goes into sleep mode.

During program mode the operator uses the manual UP and DOWN switches 146, 148 or the system's normal operator switching mechanism 14 to flex or extend the actuator to the first position to be programmed into memory as a designated stop position. As the actuator articulates in the program mode the current position register within the local controller 60 is incremented or decremented so that its value describes the position of the actuator. When the operator finds a first position to be recorded, the program button 114 is depressed. The operator repeats the procedure to program in up to 8 stop positions.

Figure 9A:
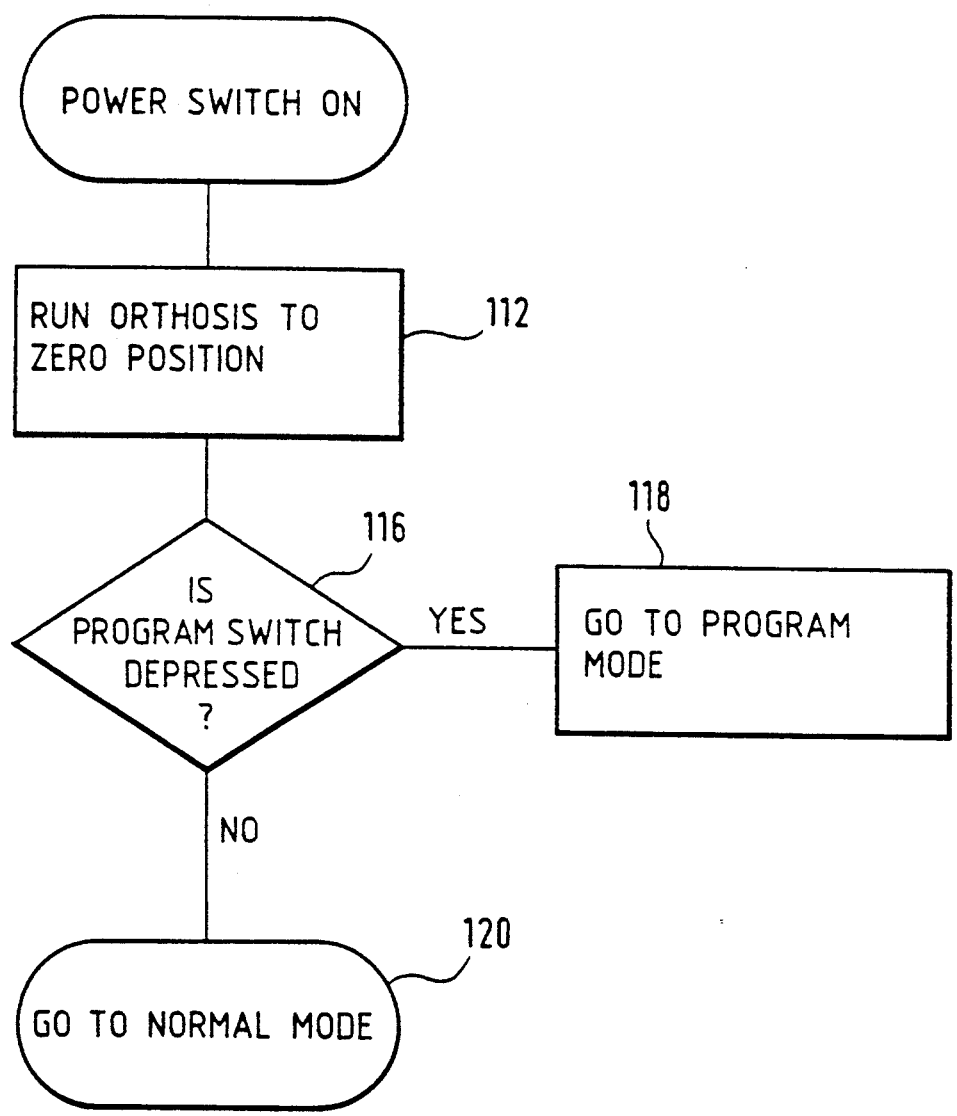
Figure 9B:
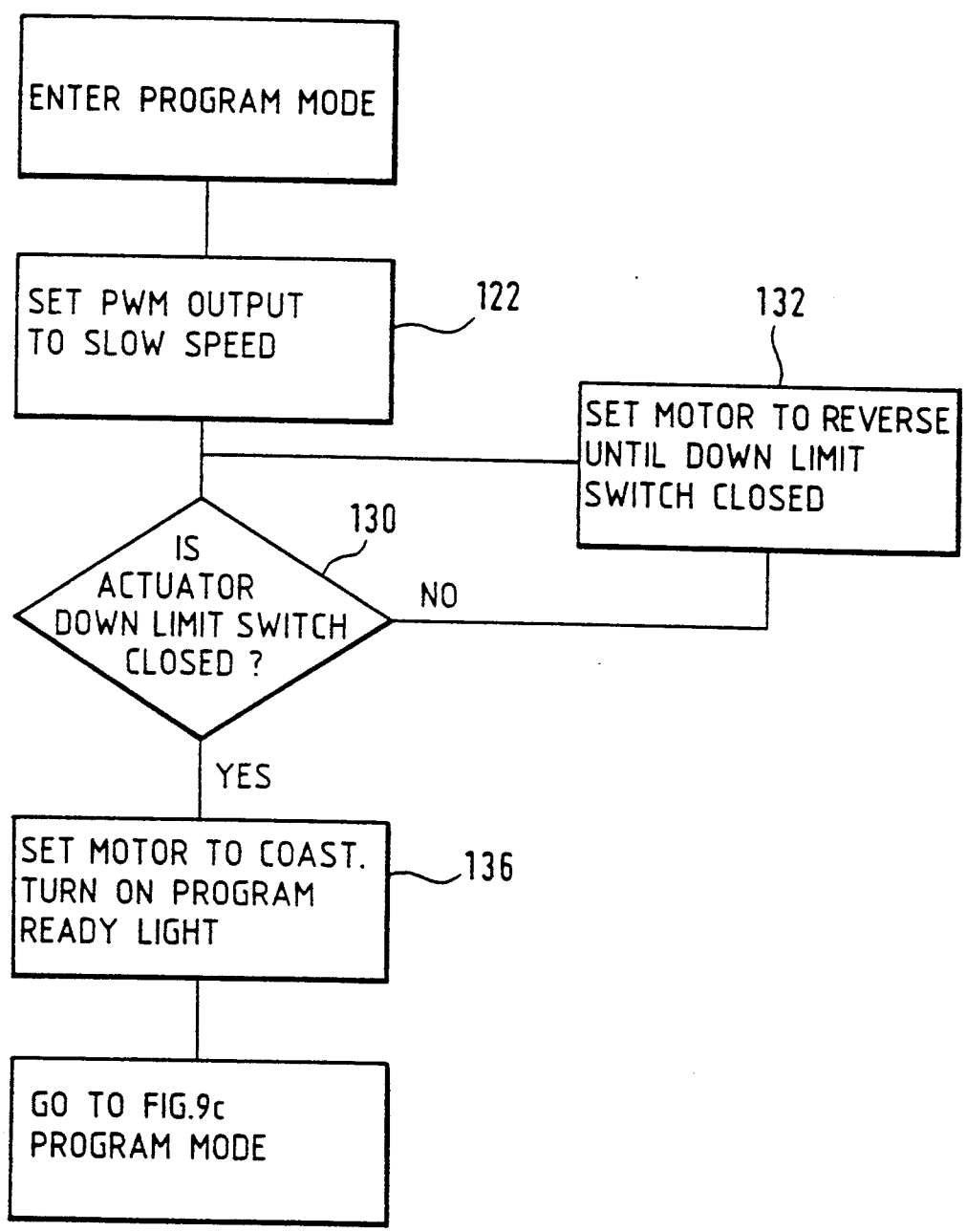

The flow charts for program mode are shown in FIGS. 9b-9e. Referring to FIGS. 6 and 9b, upon entering program mode step 122 is executed causing microcontroller 60 to set the pulse width modulation for slow speed drive of the motor 64. Referring to FIG. 6, the signal from the local controller 60 is output to power transistor 126 and then filter circuit 128. The filter circuit 128 changes the pulsating dc signal to a smooth dc voltage proportional to the "on" time of the PWM pulses. The motor controller 124 routes the dc voltage from the PWM filter 128 to the appropriate leads of motor 64 to cause rotation in the correct direction or to cause braking. Step 130, then is executed at which the down limit switch 92' (full extension sensor) is read to determine if the actuator is at the full extension position. If not, the motor controller 124 is placed in the reverse mode at step 132 until the down limit switch is closed. The down limit switch 92' is polled until the actuator is fully extended to the "zero" or reference position, at which time the motor controller 124 is returned to coast. When the limit is detected, the "PROGRAM" LED 134 is turned on at step 136.

Figure 9C:
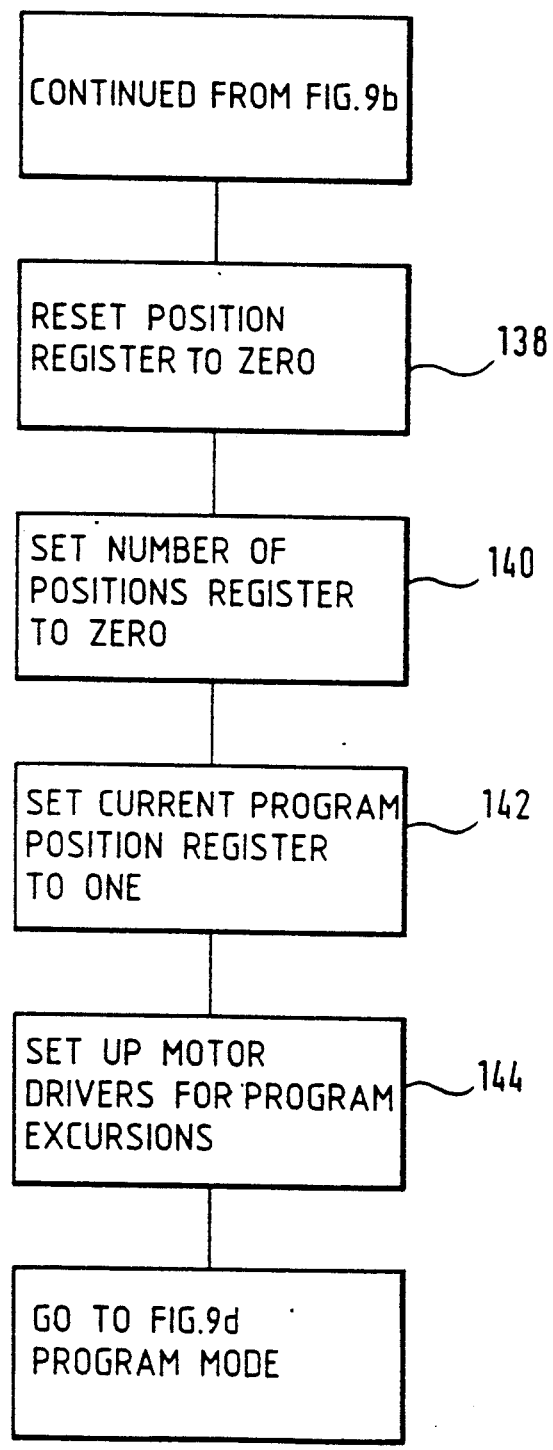

Referring to FIG. 9c, the actuator position register then is reset for the "zero" position at step 138 and the number of stop positions register is reset to zero at step 140. Thus, by pressing the program buttons the old stop positions are lost. At step 142 the current position register is set to one. At step 144, the motor drive is set for ensuing motor commands.

Figure 9D:
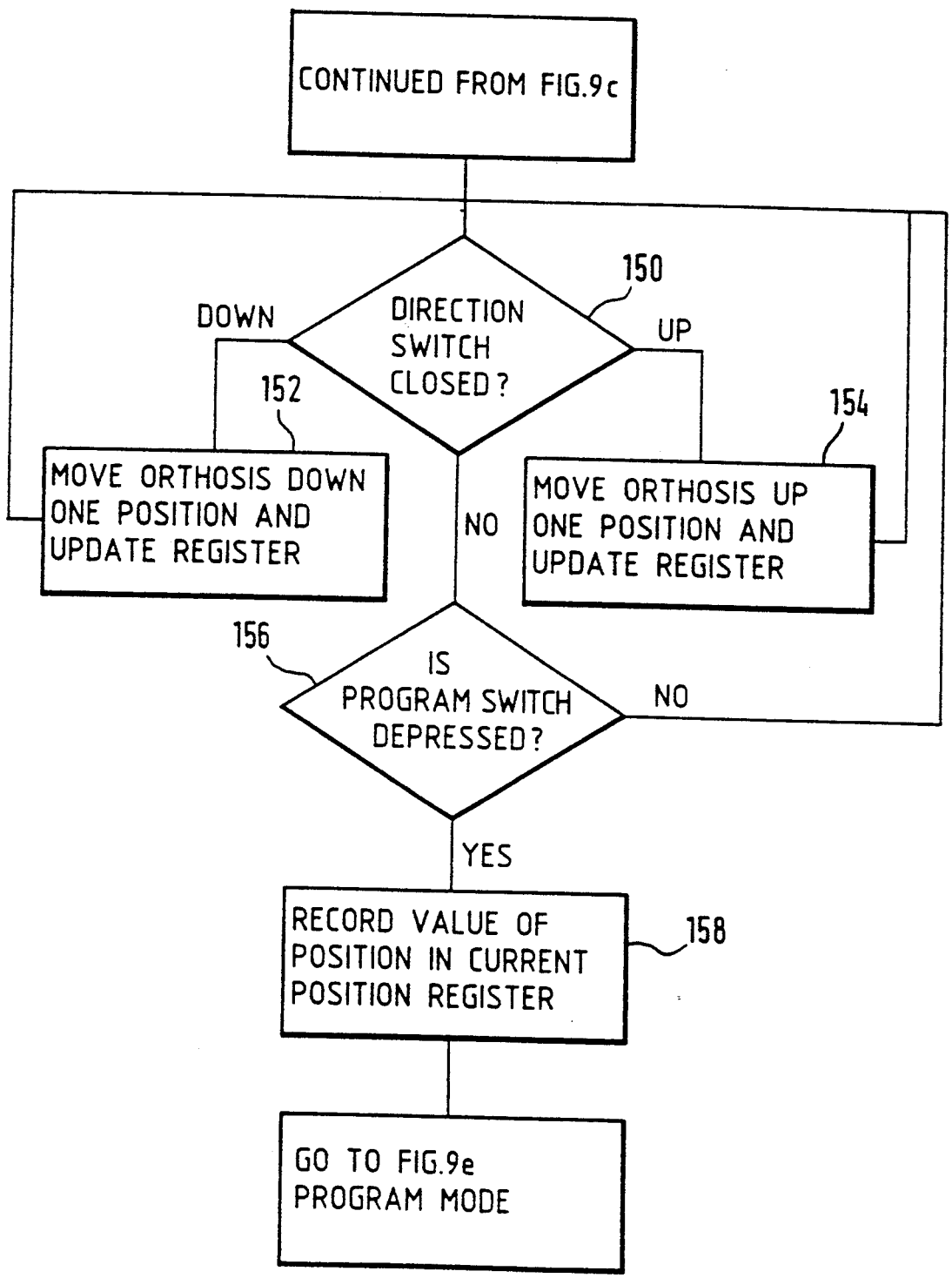
Figure 9E:
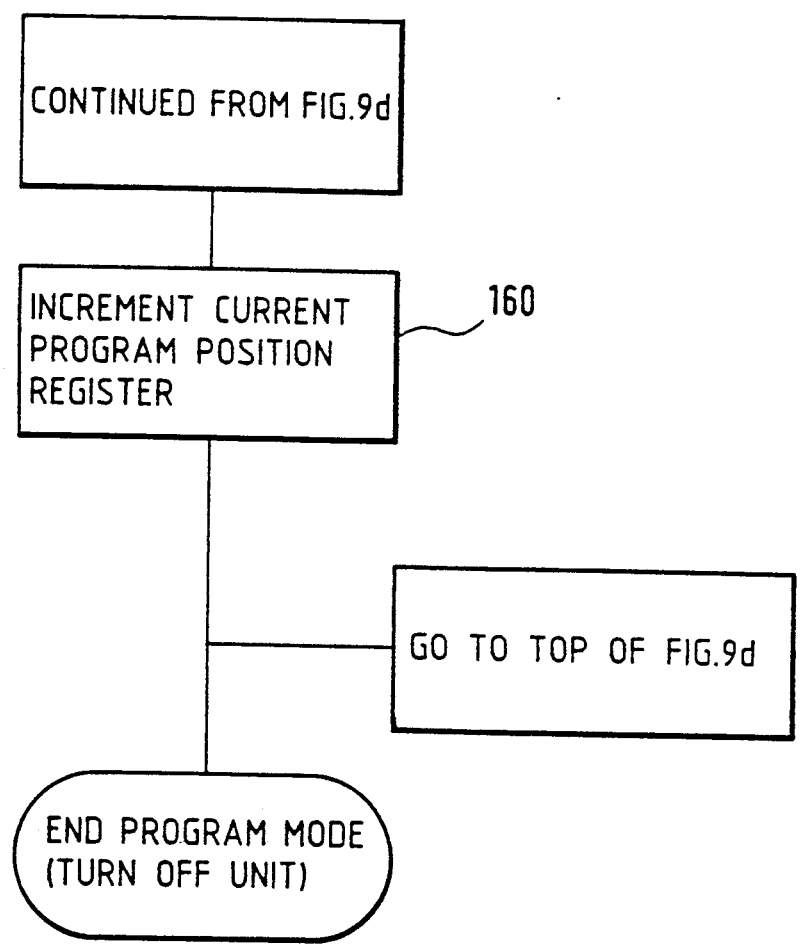

Referring to FIGS. 1, 6 and 9d, the manual up switch 146 and manual down switch 148 of the local subsystem 44 are polled at step 150. If the up switch 146 is closed, the actuator 62 is moved up one position and the current position register is updated at step 154. If the down switch 148 is closed, the actuator 62 is moved down one position and the current position register is updated at step 152. Then, the manual up and manual down switches are repolled by reexecuting step 150. When neither switch is closed the program switch 114 is polled at step 156. If it is not depressed the manual up and manual down switches are re-polled by reexecuting step 150. If the program switch 114 is depressed, the value in the current position register is received in nonvolatile memory 157 as a stop point at step 158. Referring to FIG. 9e, the current position register then is incremented at step 160. Referring back to FIG. 9d, step 150 then is reexecuted. The polling of the manual up switch 146, manual down switch 148 and program switch 114 in learn mode continues until the power switch 110 is turned off. When the power switch 110 is shut off the current position and the stop points are saved in non-volatile memory.

When programming in the "program mode", the local controller 60 controls the speed of the motor 64 to run much slower than during normal operation. The slow speed enables the user to accurately reach the desired flexion-extension point and program that value as a stop point. However, when in the "program mode" the motor 64 will increase in speed as the distance of travel from the previous stopping point increases. From full extension to full-flexion the motor's rpm will increase two to three times. The parameters for minimum and maximum lead screw 78 rpm during learn mode are 30 rpm and 100 rpm.

To operate the apparatus 10 in a normal mode, the power switch 110 is turned back on and the initialization of FIG. 9a is reexecuted. As a result, the actuator is returned to the software zero position at step 112. During normal operation the program switch 114 would not be depressed. Thus, the local controller 60 would go into sleep mode at step 120.

Figure 9F:
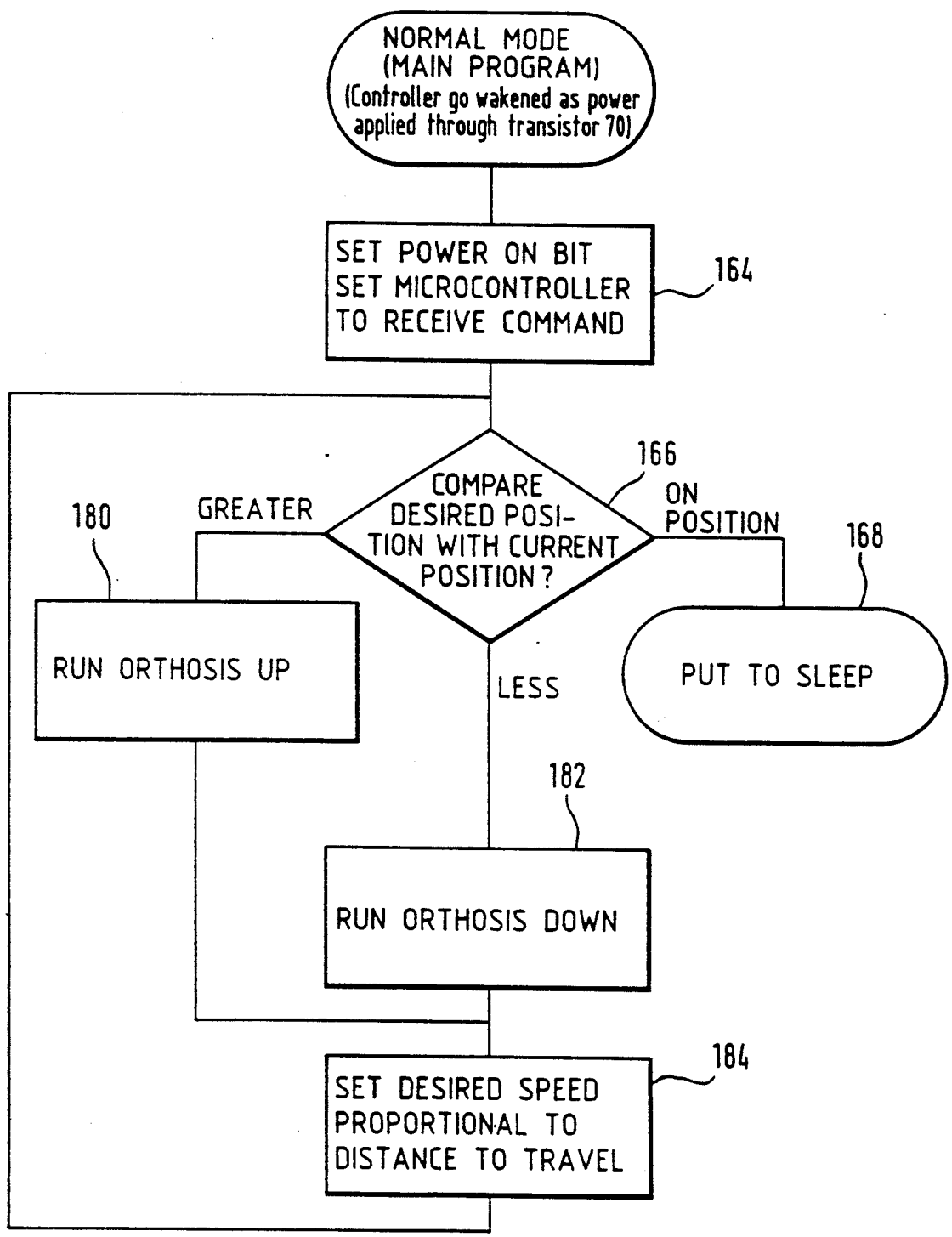

Referring to FIG. 9f, in sleep mode a power on bit (P16 of controller 60 in FIG. 6) is set to hold power transistor 162 on at step 164 and the local controller 60 is set to receive commands from the receiver 58. At step 166, the desired position is compared with the current position, which initially will be the same, namely the zero position. Thus, the local controller 60 executes step 168 and puts itself to sleep by resetting the power on bit, thereby turning off its own power.

When a radio signal is received the controller 60 is awakened via power switching transistor 170 (see FIG. 6). At step 166, the desired position is compared to the current position. If greater, step 180 is executed causing the actuator to move in the flexion direction. If less, step 182 is executed causing the actuator to move in the extension direction. The desired motor speed then is set at step 184 in proportion to the distance to travel. In addition, "TO" is tested by the timer interrupt routine (FIG. 9h) which is executed every 37.5 microseconds while controller 60 is in a wakened state. At step 172 therein, the encoded digital data is read into the controller 60 for processing at a rate of 1 bit per 28 interrupts. At step 174 the serial number is checked and the data is deciphered to determine whether an up command or down command is requested. If an up command is requested, the desired position register is incremented to correlate to the next stop position in the flexion direction and the direction bit is reset at step 176. If a down command, the desired position register is decremented to correlate to the next stop position in the extension direction and the direction bit set at step 178. At step 179 the motor speed register is incremented every 28 interrupts. With the register initially zero, the register functions as a counter to define the motor speed.

The motor speed is determined by the photo interrupt routine of FIG. 9g which also clears the speed register for the next speed determination.

At step 181, over the duration of 28 timer interrupts a pulse width modulated signal is developed by comparing the number of timer interrupts (0–27) with the value in the PWM register in the accumulator of controller 60. If the value is equal, P10 is turned on causing the PWM output transistor to be turned on. P10 will be reset to an off state on the 28th interrupt. This allows a signal with a period of approximately 1 millisecond to be generated at P10 with a duty cycle ranging from over 95% (PWM register=0) to 0% (PWM register=27) in 28 steps to be sent to the PWM output transistor 126. This provides 28 available voltages to the motor. If desired, other timing routines may be used. The interrupt routine then returns program control to the main program (FIG. 9f) until the next timer interrupt or until the subsystem 44 is put to sleep. Controller 60 is awakened when the receiver 58 receives a starting bit and causes transistor 70 to apply power to the local controller 60. At Step 164 the power on bit is set (P16 of controller 60 in FIG. 6) to hold power transistor 162 on and the timer interrupt is enabled allowing the controller 60 to receive commands from receiver 58. The program interrupt routine (FIG. 9g) also is enabled so that changes in position can be detected.

While the controller 60 is executing in the loop of FIG. 9f, the actuator is moving causing the photo interrupter sensors to generate interrupts in the form of pulse trains caused by the sequential breaking of light circuits by the encoder wheel 108. The flow chart for the photo interrupt routine is shown in FIG. 9g. At step 186, the direction bit is polled to determine whether the actuator is moving up or down. If up (i.e. direction bit reset), the current position register is incremented at step 188. If down (i.e. direction bit set), the current position register is decremented at step 190. The actual speed is based on the time since the last interrupt and the known arc distance between holes or reflective surfaces on the encoder wheel. At step 192, the speed register is compared to the desired speed. If approximately equal the PWM register is left unchanged. If different, the PWM register is incremented or decremented to increase or decrease the motor drive. The PWM register is periodically read by the timer interrupt routine to adjust the pulse width modulation so as to control the speed of motor 64. The speed register is reset at step 194. The interrupt routine then ends returning program control to the loop in FIG. 9f.

The loop continues until the desired position equals the current position causing the controller 60 to execute step 168 and reset the power on bit (P16) thereby turning off its own power and putting itself to sleep.

For each time the operator switching mechanism is activated, the local controller 60 will cause the desired position to increment or decrement to the next stop position in the direction of movement. For example, if the operator switching mechanism 14 is activated twice to move the brace up (increase flexion), the actuator 62 will smoothly move the angle of the of the orthosis two programmed stopping points. The actuator 62 will move at normal speed past the undesired stop position(s) until it brakes to a stop at the desired position.

Referring to FIG. 6, a liquid crystal display 189 provides a digital readout of the degree of flexion or extension of the orthosis, prosthesis or CPM machine.

With regard to the power sources,, one power supply 109 from switch 110 of FIG. 6 powers the radio receiver 58. This power supply 109 puts out a few milliamps at all times apparatus 10 is on, whether awakened or in sleep mode.

A voltage regulator 200 (see FIG. 6) regulates the power supply 109 to supply a regulated 5 volts to the local controller 60, the static CMOS-RAM 157, and the motor controller integrated circuit 124. This power supply is activated by the radio receiver 58 as the receiver senses a transmission signal. The regulator 200 is latched in the ON state by a bit (P16) from the local controller 60. This power supply is deactivated during sleep mode to conserve power.

The power supply 109 through PWM output transistor 126 and filter 128 provides the voltage that drives the motor 64. This voltage is variable depending on how fast the motor needs to be driven. The signal that controls the voltage is the PWM drive voltage signal from the local controller 60.

Another power supply is a coin-type three volt battery 201 (see FIG. 6) that keeps the CMOS-RAM 157 alive when the power switch 110 is off or the local subsystem 44 is in sleep mode.

The range of motion apparatus as an orthotic device is shown in FIGS. 10a-b, with an orthotic upper arm brace 210 and forearm brace 212.

Figure 11:
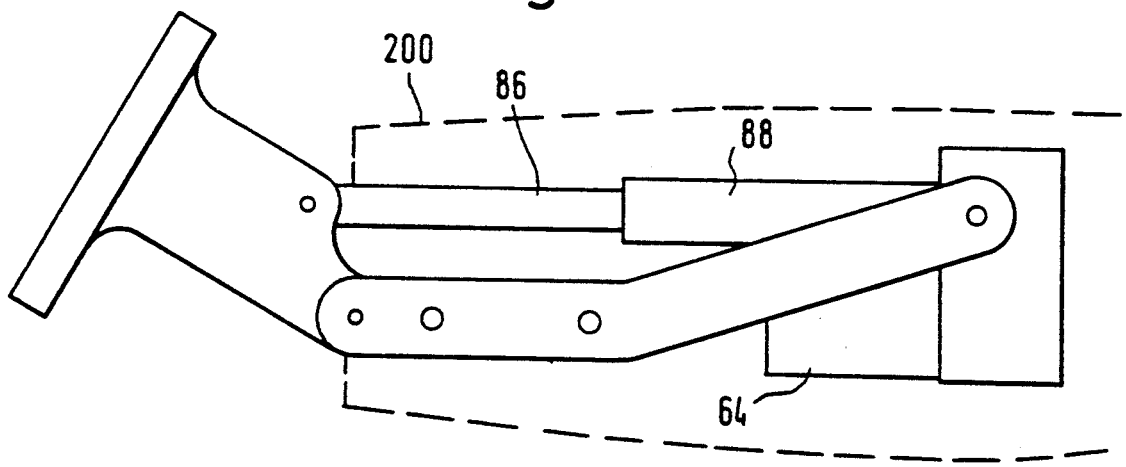
FIG. 11 is a perspective view of an above-elbow prosthesis embodiment of this invention.

Another embodiment of the range of motion apparatus 10 is shown in FIG. 11 as an above-elbow prosthesis to provide an amputee the same programming features, multiple range options, and wireless control that the apparatus 10 offers for orthotics patients. When applied prosthetically, the apparatus 10 is housed in the hollow exoskeletal forearm section of the prosthesis 200. The end of the ram 86 is affixed inside the humeral section of the prosthesis at an appropriate pivot point.

Figure 12:
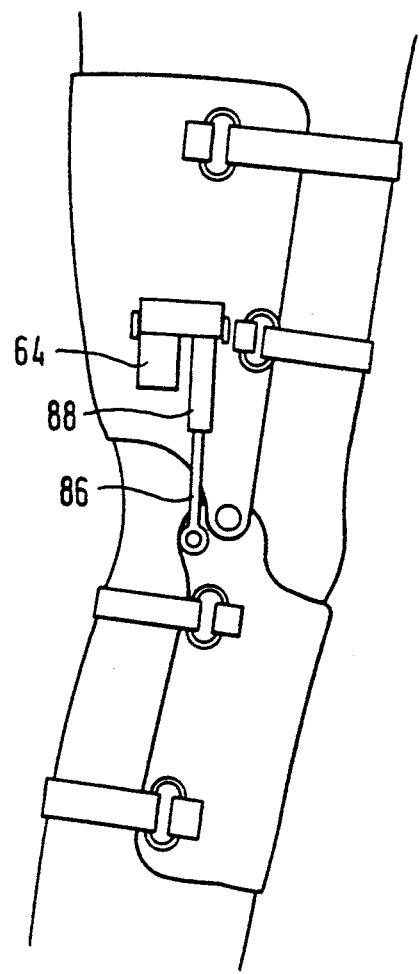
FIG. 12 is a perspective view of a CPM machine embodiment of this invention for a knee joint.

Apparatus 10 also may be embodied for a Continuous Passive Motion (CPM) machine application for (see FIG. 12) joints such as the elbow, knee (flexion-extension), ankle (dorsiflexion-plantarflexion) or wrist (flexion-extension or rotation).

The CPM embodiment accepts only one up stopping point and one down stopping point. To set the desired flexion-extension stops, the user depresses the up button 146 for flexion and the down button 148 for extension, stops the brace at the desired degree and inputs that stop using either the up or down "Enter Stops" buttons 210, 212. After the stopping points are programmed, the user depresses a start button 208 to begin operation.

As the user depresses either of the Manual Position buttons, the brace will flex or extend accordingly and the degree of flexion-extension will be displayed on the left side of the LCD display. The flexion-extension stops are erased when the user programs in new stops.

Figure 13:
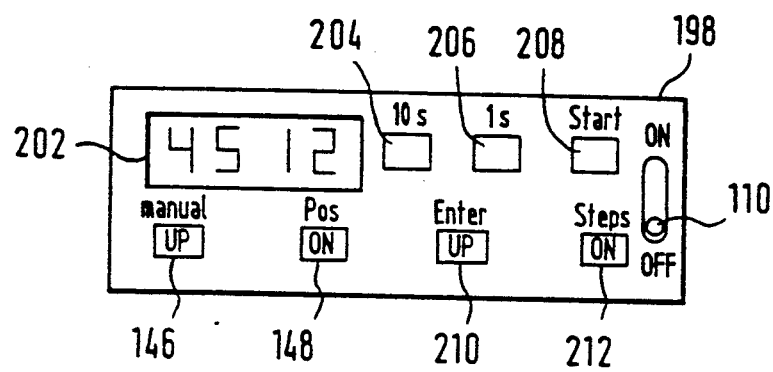
FIG. 13 is a diagram of a control panel for a CPM machine embodiment.

A control panel 198 (see FIG. 13) for the CPM embodiment includes liquid crystal display (LCD) 202 having two sets of digits. One set of digits indicates the position (degree of flexion-extension) of the actuator. The other set indicates how many programmed repetitions the user desires to perform. The user programs in the number of repetitions by depressing the 10's and 1's buttons 204, 206 on the panel.

Figure 14:
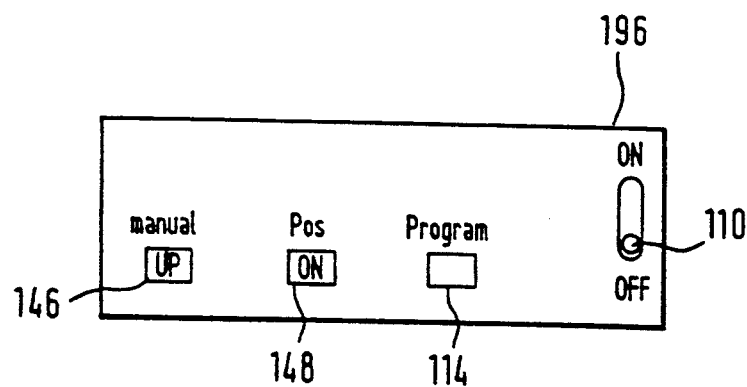
FIG. 14 is a diagram of a control panel for the orthosis and prosthesis embodiments of this invention.

Referring to FIG. 14, the orthosis and prosthesis embodiments may include a control panel 196 at which the power switch 110, program switch 114, manual up switch 146 and manual down switch 148 are located.

While preferred embodiments of the invention have been illustrated and described, the invention is not intended to be limited to the exact embodiments illustrated.

We claim:

1. A portable therapeutic electronic range of motion apparatus to be worn and operated by a patient, comprising:
    an upper brace and a lower brace positioned on a patient's upper joint area and lower joint area respectively, said areas being proximate to a joint;
    a housing having an actuator sized and configured to be attached to said upper brace, said actuator having an extendable ram disposed in said housing, one end of said ram being connected to said lower brace for extending and flexing the joint, said actuator being responsive to a motor disposed in said housing, actuator movable over a range of positions;
    an operator switching mechanism for generating a motion command;
    a digital processor within said housing responsive to said operator switching mechanism for receiving and processing said motion command, said actuator movable under the control of said digital processor;
    memory means within said housing, controlled by said digital processor for receiving and storing information representing selected discrete stopping positions of the actuator, said actuator movable among said stored selected stopping positions in response to said motion command generated by the operator switching mechanism;
    calculator within said housing for determining instantaneous distance of the actuator to a selected stopping position by comparing said selected stopping position with actual position of the actuator; and
    speed controller disposed within said housing and responsive to said calculator, said speed being a function of said instantaneous distance.

2. The invention according to claim 1, wherein said memory means stores information representing a first and a second stopping position respectively for a desired flexion and extension position, said actuator ram moving back and forth between said first and second stopping positions causing controlled extension and flexion of said joint.

3. The apparatus as claimed in claim 2 wherein said actuator includes a lead screw received into a first end of said ram within a ram housing, the second end of said ram receiving a heim ball joint for attaching to said lower brace, said lead screw adaptable to turn at a variable speed to extend and flex said ram, moving said lower brace.

4. The apparatus as claimed in claim 3 wherein said upper brace is an arm brace and said lower brace is a forearm brace positioned on a patient's arm and forearm and said joint extending and flexing is a patient's elbow.

5. The apparatus as claimed in claim 4, wherein said means for controlling the speed of the actuator sets the speed proportional to said instantaneous distance so as to gradually slow the movement of the actuator as it nears said selected stopping position.

6. The apparatus as claimed in claim 3, wherein said upper brace is an upper leg brace and said lower brace is a lower leg brace positioned on a patient's upper and lower leg and said joint extending and flexing is a patient's knee.

7. The apparatus as claimed in claim 6, wherein said means for controlling the speed of the actuator sets the speed proportional to said instantaneous distance so as to gradually slow the movement of the actuator as it nears said selected stopping position.

8. The apparatus as claimed in claim 1, wherein said operator switching mechanism for generating a motion command is remotely disposed from said housing.

9. A portable therapeutic electronic range of motion apparatus to be worn and operated by a patient, comprising:
    an upper brace and a lower brace positioned on a patient's upper joint area and lower joint area respectively, said areas being proximate to a joint;
    a housing having an actuator sized and configured to be attached to said upper brace, said actuator having an extendable ram disposed within said housing, one end of said ram being connected to said lower brace for extending and flexing the joint said actuator movable over a range of positions;
    an operator switching mechanism for generating a motion command;
    a digital processor within said housing for receiving and processing the motion command, said actuator movable under the control of said digital processor;
    calculator within said housing for determining instantaneous distance of the actuator to a selected stopping position by comparing said selected stopping position with actual position of the actuator;
    means for controlling the speed of the actuator disposed within said housing and responsive to said calculator to set the speed proportional to said instantaneous distance so as to gradually slow down the actuator when approaching a stopping position;
    means for automatically switching off power to the digital processor and actuator after a stopping position is reached; and
    means for automatically restoring power to the digital processor and actuator in response to a motion command generated from said operator switching mechanism.

10. The apparatus of claim 9, further comprising means for storing information representing selected discrete stopping positions available from a plurality of selectable stopping positions of the actuator within the range of positions which thereafter are selectable by a motion command of the operator switching mechanism said stopping positions being actual positions of the actuator; and means for retaining the stopping positions while power is off.

11. A portable therapeutic electronic range of motion apparatus, comprising:
- a remote subsystem comprising an operator switching mechanism for generating a motion command, the remote subsystem transmitting the motion command;
- a local subsystem to be worn and operated by a patient comprising a housing having means for receiving the transmitted motion command, a processing means within said housing for processing the motion command, an upper brace and a lower brace positioned on a patient's upper joint area and lower joint area, said areas being proximate to a joint;
- an actuator sized and configured within said housing to be attached to said upper brace, said actuator having an extendable ram within said housing, one end of said ram being connected to said lower brace for extending and flexing the joint said actuator movable over a range of positions, a motor controlled by the processing means for moving the actuator in response to a motion command generated by said operator switching mechanism, means for automatically switching off the power to the processing means and motor when the actuator is not in motion, and means for automatically restoring power to the processing means and motor in response to a motion command generated by said operator switching mechanism;
- means within said housing for storing information representing desired actual positions where actuator stops, said actual positions are selectable by a motion command generated by the operator switching mechanism, wherein the patient (1) activates a programming mode of the processing means causing the actuator to move to a reference position, (2) generates a motion command to automatically move the actuator from the reference position, and (3) generates a program command causing the current actual position of the actuator to be stored as a stopping position;
- calculating means within said housing for determining instantaneous distance of the actuator to a selected stopping position by comparing said desired stopping position with actual position of the actuator; and
- wherein the processing means processes the motion command by causing the motor to move the actuator at a speed proportional to said instantaneous distance while monitoring the movement of the actuator.

12. A method for a patient for using a portable therapeutic electronic range of motion apparatus to be worn and operated by the patient, comprising the steps of:
- activating a programming mode of the apparatus;
- positioning an upper brace and a lower brace on a patient's upper joint area, and lower joint area, said areas being proximate to a joint;
- automatically moving an actuator of the apparatus to a reference position, in response to said step of activating said programming mode, said actuator disposed in a housing being attached to said upper brace, and having an extendable ram, one end of said ram being connected to said lower brace for extending and flexing the joint;
- moving the actuator from the reference position to desired positions in response to a motion command generated by the patient;
- storing information representing said desired positions of the actuator as desired stopping positions in response to a program command generated by the patient;
- activating a motion command mode of the apparatus;
- moving the actuator to said desired stopping positions previously stored, in response to said motion command mode;
- calculating instantaneous distance of the actuator to said desired stopping position by comparing said desired stopping position with actual position of the actuator; and
- controlling the speed of the actuator to set the speed proportional to said instantaneous distance so as to gradually slow down the actuator when approaching a desired stopping position.

* * * * *